United States Patent [19]

Daute et al.

[11] Patent Number: 5,237,080
[45] Date of Patent: Aug. 17, 1993

[54] ALKOXYLATION PRODUCTS OF OH-FUNCTIONAL CARBOXYLIC ACID DERIVATIVES AND/OR CARBOXYLIC ACIDS

[75] Inventors: Peter Daute, Essen; Gerhard Stoll, Korschenbroich, both of Fed. Rep. of Germany

[73] Assignee: Henkel Kommanditgesellschaft auf Aktien, Duesseldorf-Holthausen, Fed. Rep. of Germany

[21] Appl. No.: 820,901
[22] PCT Filed: Jul. 10, 1990
[86] PCT No.: PCT/EP90/01121
§ 371 Date: Jan. 14, 1992
§ 102(e) Date: Jan. 14, 1992
[87] PCT Pub. No.: WO91/01291
PCT Pub. Date: Feb. 7, 1991

[30] Foreign Application Priority Data

Jul. 14, 1989 [DE] Fed. Rep. of Germany ....... 3923394

[51] Int. Cl.⁵ .............................................. C07C 59/00
[52] U.S. Cl. ..................................... 554/213; 554/149
[58] Field of Search .................. 554/149, 213, 227; 514/558

[56] References Cited

U.S. PATENT DOCUMENTS

| | | | |
|---|---|---|---|
| 4,615,837 | 10/1986 | Abel et al. | 554/213 |
| 4,699,998 | 10/1987 | Green | 554/149 |
| 4,897,225 | 1/1990 | Biehm et al. | 554/149 |
| 5,055,230 | 10/1991 | Clubley et al. | 554/213 |

*Primary Examiner*—José G. Dees
*Assistant Examiner*—D. D. Carr
*Attorney, Agent, or Firm*—Ernest G. Szoke; Wayne C. Jaeschke; Henry E. Millson, Jr.

[57] ABSTRACT

Alkoxylation products of at least one of ethylene oxide, propylene oxide, and butylene oxide and at least one $C_{10-22}$ carboxylic acid mono-, di-, or tri-glyceride which is of natural origin or is obtained from natural origin wherein in the 9, 10 position, the 13, 14 position, or in both positions of the carboxylic acid the following unit is present

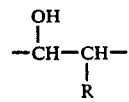

in which
R is a hydrogen atom, an OH group or an $OR^1$ group,
$R^1$ is a $C_{9-18}$ alkyl group, a $C_{9-18}$ alkenyl group or a

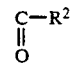

group, and
$R^2$ is a hydrogen atom, a $C_{1-21}$ alkyl group or a $C_{2-21}$ alkenyl group.

The invention also relates to compositions containing the above alkoxylation products in place of alkoxylated castor oil normally present in the compositions, and to a process for preparing the alkoxylation products.

17 Claims, No Drawings

ALKOXYLATION PRODUCTS OF OH-FUNCTIONAL CARBOXYLIC ACID DERIVATIVES AND/OR CARBOXYLIC ACIDS

This invention relates to alkoxylation products of OH-functional $C_{10-22}$ carboxylic acid derivatives and/or OH-functional $C_{10-22}$ carboxylic acids and to a process for the production of these alkoxylation products.

Ethoxylated and/or propoxylated castor oils are used, for example, in cosmetic preparations, detergents and lubricating oils and as antistatic agents for nylon carpets (Kirk-Othmer: "Encyclopedia of Chemical Technology", Vol. 5, page 9, John Wiley, New York (1979)). Where ethoxylated and/or propoxylated castor oils are used, however, it has to be accepted that the quantities of castor oil and hence ethoxylated and/or propoxylated castor oils available on the market are subject to considerable fluctuations. Poor harvests in the main growing areas of Brazil and India lead to a shortage of the starting material, castor oil, at more or less long intervals. Accordingly, there is a need for an equivalent substitute for alkoxylated castor oils. Above all, the substitute product should be accessible from a broader and less crisis-prone raw material base and should be both ecologically and toxicologically safe.

It has now been found that certain OH-functional carboxylic acids and/or OH-functional carboxylic acid derivatives alkoxylated with alkylene oxides can be used as a substitute for alkoxylated castor oils.

Accordingly, the present invention relates to alkoxylation products obtainable by reaction of ethylene oxide, propylene oxide and/or butylene oxide with $C_{10-22}$ carboxylic acid derivatives and/or $C_{10-22}$ carboxylic acids containing carboxylic acid functions which, in the 9,10 and/or 13,14 position, contain structural units corresponding to the following general formula

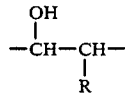

in which
R is a hydrogen atom, an OH group or an $OR^1$ group,
$R^1$ is a $C_{1-18}$ alkyl group, a $C_{2-18}$ alkenyl group or a

group or, where the corresponding mono-, di- and/or triglycerides are used as the $C_{10-22}$ carboxylic acid derivatives, $R^1$ is a $C_{9-18}$ alkyl group, a $C_{9-18}$ alkenyl group or a

group and
$R^2$ is a hydrogen atom a $C_{1-21}$ alkyl group or a $C_{2-21}$ alkenyl group.

The present invention also relates to a process for the production of alkoxylation products, characterized in that $C_{10-22}$, carboxylic acid derivatives and/or $C_{10-22}$ carboxylic acids containing carboxylic acid functions which, in the 9,10 and/or 13,14 position, contain structural units corresponding to the following general formula

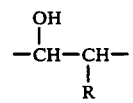

in which
R is a hydrogen atom, an OH group or an $OR^1$ group,
$R^1$ is a $C_{1-18}$ alkyl group, a $C_{2-18}$ alkenyl group or a

group or, where the corresponding mono-, di- and/or triglycerides are used as the $C_{10-22}$ carboxylic acid derivatives, $R^1$ is a $C_{9-18}$ alkyl group, a $C_{9-18}$ alkenyl group or a

group and
$R^2$ is a hydrogen atom, a $C_{1-21}$ alkyl group or a $C_{2-21}$ alkenyl group,
are reacted with ethylene oxide, propylene oxide and/or butylene oxide at temperatures of 110 to 200° C. and under pressures of $10^5$ to $2·10^6$ Pa.

The alkoxylation products according to the invention may be prepared by standard organic synthesis methods. Suitable starting materials for alkoxylated OH-functional $C_{10-22}$ carboxylic acids are any OH-free, unsaturated $C_{10-22}$ carboxylic acids of natural and/or synthetic origin containing at least one or two double bonds in the 9 and/or 13 position, for example 9c-dodecenoic acid, 9c-tetradecenoic acid, 9c-hexadecenoic acid, 9c-octadecenoic acid, 9t-octadecenoic acid, 9c,12c-octadecadienoic acid, 9c,12c,15c-octadecatrienoic acid, 9c-eicosenoic acid and/or 13c-docosenoic acid, and/or mixtures having at least a high content of such unsaturated carboxylic acids. Preferred educts are carboxylic acids containing 16 to 22 carbon atoms and at least one or two double bonds in the 9 and/or 13 position or carboxylic acid mixtures having at least a high content of carboxylic acids containing 16 to 22 carbon atoms and at least one or two double bonds in the 9 and/or 13 position.

Suitable educts for alkoxylated OH-functional $C_{10-22}$ carboxylic acid derivatives are any OH-free, unsaturated, naturally occurring and/or synthetically obtainable $C_{10-22}$ carboxylic acid derivatives containing carboxylic acid functions with at least one or two double bonds in the 9 and/ or 13 position. Examples of unsaturated carboxylic acid functions containing 10 to 22 carbon atoms are the carboxylic acids mentioned above. Unsaturated carboxylic acid derivatives containing $C_{16-22}$ carboxylic acid functions with at least one or two double bonds in the 9 and/or 13 position are preferred. Suitable unsaturated $C_{10-22}$ carboxylic acid derivatives are, for example, unsaturated $C_{10-22}$ carboxylic acid esters, unsaturated $C_{10-22}$ carboxylic acid amides, unsaturated $C_{10-22}$ carboxylic acid mono- and/or di-$C_{1-4}$-alkylamines and/or unsaturated $C_{10-22}$ carboxylic acid mono- and/or di-$C_{1-4}$-alkanolamides. Unsaturated $C_{10-22}$ carboxylic acid alkyl esters containing 1 to 18 carbon atoms in the monohydric alcohol radical and/or mono-, di- and/or triglycerides containing $C_{10-22}$ carboxylic acid functions with at least one or two double bonds in the 9 and/or 13 position are preferred.

Examples of unsaturated $C_{10-22}$-carboxylic acid-$C_{1-18}$-alkyl esters, which may be obtained in known manner by esterification of the corresponding unsaturated carboxylic acids or by transesterification of the corresponding mono-, di- and/or triglycerides with $C_{1-18}$ alkyl alcohols, for example methanol, ethanol, propanal, butanol, isobutanol, 2-ethyl hexanol, decanol and/or stearyl alcohol, are palmitoleic acid methyl ester, oleic acid methyl ester, oleic acid ethyl ester, oleic acid isobutyl ester, oleic acid-2-ethylhexyl ester and/or oleic acid decyl ester and/or $C_{10-22}$ carboxylic acid-$C_{1-18}$-alkyl ester mixtures having at least a high content of $C_{10-22}$-carboxylic acid-$C_{1-18}$-alkyl esters which, in the carboxylic acid functions, contain at least one or two double bonds in the 9 and/or 13 position, such as palm oil ethyl ester, soybean methyl ester, rapeseed oil methyl ester and/or tallow fatty acid ethyl ester. Suitable mono-, di- and/or triglycerides containing OH-free, unsaturated $C_{10-22}$ carboxylic acid functions with at least one or two double in the 9 and/or 13 position are, in particular, fats and/or oils of natural origin of which the carboxylic acid content is made up predominantly of unsaturated $C_{10-22}$ carboxylic acids containing at least one or two double bonds in the 9 and/or 13 position and, preferably, predominantly of unsaturated $C_{16-22}$ carboxylic acids containing at least one or two double bonds in the 9 and/or 13 position, such as olive oil, linseed oil, sunflower oil, safflower oil, soybean oil, peanut oil, cottonseed oil, rapeseed oil rich and/or poor in erucic acid, palm oil, lard and/or tallow.

The unsaturated $C_{10-22}$ carboxylic acid derivatives and/or unsaturated $C_{10-22}$ carboxylic acids are epoxidized by reaction with peracetic acid in the presence of acidic catalysts or with performic acid formed in situ from formic acid and hydrogen peroxide, for example in accordance with DE-PS 857 364. The epoxidation products obtained have iodine values below 20 and preferably below 15.

The oxirane rings of the epoxidized carboxylic acid derivatives and/or carboxylic acids are then opened by reaction with hydrogen or protic compounds, such as water, linear and/or branched alkyl and/or alkenyl alcohols or linear and/or branched, saturated and/or unsaturated $C_{1-22}$ carboxylic acids, with formation of hydroxy groups. The ring-opening conditions are selected so that the acid derivative and acid groups remain intact.

The hydrogenation of epoxidized carboxylic acid derivatives and/or epoxidized carboxylic acids may be carried out, for example, by the process described in DE-OS 20 21 530 in the presence of catalysts based on heavy metals of the VIIIth group of the periodic system at temperatures in the range from 100 to 250° C. and under hydrogen pressures of $10^6$ to $5 \cdot 10^6$ Pa.

The reactions of epoxidized carboxylic acid derivatives and/or epoxidized carboxylic acids with protic compounds may be carried out by the processes described in M. S. Malinovskii "Epoxides and their Derivatives", Sivon Press, 1965, at temperatures in the range from 50 to 200° C. and under pressures of $10^5$ to $10^6$ Pa. Ring-opening reactions with linear and/or branched alkyl and/or alkenyl alcohols are preferably carried out in the presence of acidic catalysts, such as sulfuric acid and/or p-toluene-sulfonic acid. Alkyl and/or alkenyl alcohols containing 9 to 18 carbon atoms are used to open the oxirane rings of epoxidized mono-, di- and/or triglycerides. The oxirane rings of all other epoxidized carboxylic acid derivatives and the oxirane rings of epoxidized carboxylic acids can be opened with $C_{1-18}$ alkyl alcohols and/or $C_{2-18}$ alkenyl alcohols.

The carboxylic acid derivatives and carboxylic acids containing carboxylic acid functions with at least one OH group in the 9, 10, 13 and/or 14 position obtainable by opening of the oxirane rings are subsequently alkoxylated by known industrial methods with ethylene oxide, propylene oxide and/or butylene oxide, preferably with ethylene oxide and/or propylene oxide, preferably in the presence of catalysts, for example potassium hydroxide and/or sodium methylate, at temperatures in the range from 110 to 200° C. and preferably at temperatures in the range from 140 to 175° C. under pressures of $10^5$ to $2 \cdot 10^6$ Pa and preferably under pressures of $3 \cdot 10^5$ to $5 \cdot 10^5$ Pa (see, for example, "Chemische Technologies", Vol. 7, pages 131 to 132, Carl-Hanser-Verlag, Munchen/Wien (1986)).

The alkylene oxide content of the OH-functional carboxylic acid derivatives and/or carboxylic acids to be alkoxylated is between 2 and 400% by weight and preferably between 40 and 200% by weight, based on the non-alkoxylated compounds.

EXAMPLES

1. Production of ethoxylated, OH-functional soybean oil from hydrogenated soybean oil epoxide 20 kg epoxidized soybean oil (approximate fatty acid composition: 8% by weight palmitic acid, 4% by weight stearic acid, 28% by weight oleic acid, 53% by weight linoleic acid and 6% by weight linolenic acid; epoxide content 6.78% by weight, iodine value 5, acid value 0.4) and 0.2 kg of a nickel catalyst (support material: kiesel-guhr) were introduced into an autoclave and, after the air present in the autoclave had been displaced by purging with nitrogen, the epoxidized soybean oil was hydrogenated at 150 to 170° C. under a hydrogen pressure of $2 \cdot 10^5$ Pa until there was no further uptake of hydrogen (approx. 6 hours). After cooling and separation of the catalyst, hydrogenated soybean oil epoxide having an OH value (OHV) of 165.8, a saponification value (SV) of 181.4, an iodine value (IV) of 8.3 and an acid value (AV) of 1 was obtained in a yield of 20 kg.

5.0 g of a 30% by weight solution of potassium hydroxide in methanol were added to 650 g of the hydrogenated soybean oil epoxide which was then heated to 100° C. in an autoclave. At this temperature, the traces of methanol present were removed by evacuation and purging with nitrogen five times. After the reaction temperature had been increased to 150° C., a total of 308 g ethylene oxide was added in portions so that the pressure in the reactor did not exceed a value of $5 \cdot 10^5$ Pa. On completion of the reaction, the reaction mixture was cooled to around 90° C. and, to remove any traces of ethylene oxide still present, the autoclave was evacuated for about 15 minutes. A clear yellow liquid having an OHV of 124.5 was obtained.

2. production of ethoxylated and propoxylated, OH-functional soybean oil from hydrogenated soybean oil epoxide 6.2 g of a 30% by weight solution of potassium hydroxide in methanol were added to 371 g of the soybean oil epoxide hydrogenated in accordance with Example 1 which was then reacted first with 440 g ethylene oxide and then—in the same reactor—with 232 g propylene oxide under the conditions described in Example 1. After removal of traces of propylene oxide in vacuo and neutralization of the catalyst with 3.3 g lactic acid, a golden yellow liquid having an OHV of 72.1 was obtained.

3. Production of ethoxylated OH-functional linseed oil from hydrogenated linseed oil epoxide 1,200 g epoxidized linseed oil (approximate fatty acid composition: 5% by weight palmitic acid, 4% by weight stearic acid, 22% by weight oleic acid, 17% by weight linoleic acid and 52% by weight linolenic acid; epoxide content 8.9% by weight, iodine value 10, acid value 0.7) and 15 g of a nickel catalyst (support material: kieselguhr) were introduced into an autoclave as in Example 1 and, after the air present in the autoclave had been displaced by purging with nitrogen, the epoxidized linseed oil was hydrogenated at 150 to 170° C. under a hydrogen pressure of 2 10⁶ Pa until there was no further uptake of hydrogen. Colourless hydrogenated linseed oil epoxide having an OHV of 202.6, an SV of 178.2, an IV of 16.9 and an AV of 0.7 was obtained after cooling and separation of the catalyst.

650 g of the hydrogenated linseed oil epoxide were reacted as in Example 1 with 308 g ethylene oxide. A yellow liquid having an OHV of 152 was obtained.

4. production of ethoxylated OH-functional soybean oil from soybean oil epoxide reacted with carboxylic acids 126 kg (805 mol) of a mixture of saturated fatty acids (60% by weight octanoic acid, 35% by weight decanoic acid, 3% by weight dodecanoic acid and 2% by weight hexanoic acid; AV 361.9, IV<1) and 180 kg (766 mol) epoxidized soybean oil (characteristic data as in Example 1) were introduced into a stirred tank reactor and heated with stirring to 170° C. When the reaction mixture was free from epoxide groups (approx. 4 hours), it was distilled in vacuo at a temperature of up to about 190° C. A dark yellow liquid having an OH value of 84.6, an SV of 239 and an AV of 2.4 was obtained.

6.9 g of a 30% by weight solution of potassium hydroxide in methanol were added to 423 g of the reaction product of soybean oil epoxide with carboxylic acids which was then reacted with 660 g ethylene oxide at 140.C as in Example 1. After removal of traces of ethylene oxide in vacuo and neutralization with lactic acid, a dark yellow liquid having an OHV of 54.7 was obtained.

5. Production of ethoxylated OH-functional soybean oil from soybean oil epoxide reacted with lauryl alcohol In a stirred tank reactor, 3.6 g concentrated sulfuric acid were added to 474 g soybean oil epoxide (characteristic data as in Example 1) and 745 g lauryl alcohol and the contents of the reactor were heated to 100° C. When the reaction mixture was free from epoxide groups (approx. 3.5 hours), it was neutralized with 3.6 g diethyl ethanolamine and the excess lauryl alcohol was distilled off at 135° C. in a vacuum of 10 Pa. 723 g of a reaction product having an OHV of 112, an IV of 20, an SV of 116 and an AV of 72 were obtained.

4.0 g of a 30% by weight solution of potassium hydroxide in methanol were added to 390 g of the reaction product of soybean oil epoxide with lauryl alcohol which was then reacted with 610 g ethylene oxide at 170° C. as in Example 1. A yellow paste was obtained after removal of traces of ethylene oxide in vacuo and neutralization with lactic acid.

We claim:

1. An alkoxylation product of a) at least one of ethylene oxide, propylene oxide, and butylene oxide, and b) at least one $C_{10-22}$ carboxylic acid mono-, di-, or triglyceride which is of natural origin or is obtained from natural origin wherein in the 9, 10 position, the 13, 14 position, or in both positions of the carboxylic acid, the following unit is present

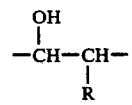

in which
R is a hydrogen atom, an OH group or an $OR^1$ group,
$R^1$ is a $C_{9-18}$ alkyl group, a $C_{9-18}$ alkenyl group or a

group, and
$R^2$ is a hydrogen atom, a $C_{1-21}$ alkyl group or a $C_{2-21}$ alkenyl group.

2. The alkoxylation product of claim 1 wherein the alkylene oxide content of the product, based on the nonalkylated glyceride, is from about 2 to about 400% by weight.

3. The alkoxylation product of claim 2 wherein the alkylene oxide content is from about 40 to about 200% by weight.

4. The alkoxylation product of claim 1 wherein the alkylene oxide is ethylene oxide, propylene oxide, or both.

5. The alkoxylation product of claim 3 wherein the alkylene oxide is ethylene oxide, propylene oxide, or both.

6. The alkoxylation product of claim 1 wherein the carboxylic acid moiety contains from 16 to 22 carbon atoms.

7. The alkoxylation product of claim 1 which is a mixture of alkoxylated glyercides.

8. The alkoxylation product of claim 1 wherein the alkylene oxide is ethylene oxide, propylene oxide, or both and the alkylene oxide content is from about 40 to about 200% by weight based on the nonalkylated glyercide, and wherein the carboxylic acid moiety contains from 16 to 22 carbon atoms.

9. In a cosmetic composition, detergent composition, lubricating oil, or antistatic agent in which alkoxylated castor oil is a component thereof, the improvement comprising the presence therein of an alkoxylation product of at least one of ethylene oxide, propylene oxide, and butylene oxide ad at least one $C_{10-22}$ carboxylic acid mono-, ci-, or tri-glyceride which is of natural origin or is obtained from natural origin wherein the 9, 10 position, the 13, 14 position, or in both positions of the carboxylic acid, the following unit is present

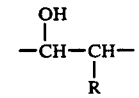

in which
R is a hydrogen atom, an OH group or an $OR^1$ group,
$R^1$ is a $C_{9-18}$ alkyl group, a $C_{9-18}$ alkenyl group or a

group, and

R² is a hydrogen atom, a C₁₋₂₁ alkyl group or a C₂₋₂₁ alkenyl group, in place of at least part of the alkoxylated castor oil content thereof.

10. The cosmetic composition, detergent composition, lubricating oil, or antistatic agent of claim 9 wherein said alkoxylation product is present in place of all of the alkoxylated castor oil content thereof.

11. The cosmetic composition, detergent composition, lubricating oil, or antistatic agent of claim 9 wherein in said alkoxylation product the alkylene oxide is ethylene oxide, propylene oxide, or both and the alkylene oxide content is from about 40 to about 200% by weight based on the nonalkylated glyceride, and wherein the carboxylic acid moiety contains from 16 to 22 carbon atoms.

12. A process for the preparation of an alkoxylation product comprising the steps of A. reacting together at a temperature in the range of from about 110 to about 200° C. and at a pressure of from about $10^5$ to about $2 \cdot 10^6$ Pa a) ethylene oxide, propylene oxide, butylene oxide, or a mixture of two or more of the above, and b) at least one C₁₀₋₂₂ carboxylic acid mono-, di-, or tri-glyceride which is of natural origin or is obtained from natural origin wherein in the 9, 10 position, the 13, 14 position, or in both positions of the carboxylic acid the following unit is present

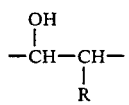

in which

R is a hydrogen atom, an OH group or an OR¹ group,

R¹ is a C₉₋₁₈ alkyl group, a C₉₋₁₈ alkenyl group or a

group, and

R² is a hydrogen atom, a C₁₋₂₁ alkyl group or a C₂₋₂₁ alkenyl group, and

B. continuing the reaction in step A until the alkylene oxide content of the product, based on component b), is from about 2 to about 400% by weight.

13. The process of claim 12 wherein step A is carried out at a temperature in the range of from about 140 to about 175° C., and at a pressure of from about $3 \cdot 10^5$ to about $5 \cdot 10^5$ Pa.

14. The process of claim 12 wherein step B is carried out until the alkylene oxide content of the product is from about 40 to about 200% by weight.

15. The process of claim 12 wherein a mixture of alkoxylation products is obtained.

16. A process for the preparation of an alkoxylation product comprising the steps of A. reacting together at a temperature in the range of from about 110 to about 200° C. and at a pressure of from about $10^5$ to about $2 \cdot 10^6$ Pa a) ethylene oxide, propylene oxide, or a mixture of the above, and b) at least one C₁₀₋₂₂ carboxylic acid mon-, di, or tri-glyceride which is of natural origin or is obtained from natural origin wherein in the 9, 10 position, the 13, 14 position, or in both positions of the carboxylic acid the following unit is present

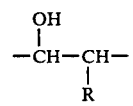

in which

R is a hydrogen atom, an OH group or an OR¹ group,

R¹ is a C₉₋₁₈ alkyl group, a C₉₋₁₈ alkenyl group or a

group, and

R² is a hydrogen atom, a C₁₋₂₁ alkyl group or a C₂₋₂₁ alkenyl group, and

B. continuing the reaction in step A until the alkylene oxide content of the product, based on component b), is from about 2 to about 400% weight.

17. The process of claim 16 wherein in Step A component b), the carboxylic acid moiety contains from 16 to 22 carbon atoms.

* * * * *

UNITED STATES PATENT AND TRADEMARK OFFICE
CERTIFICATE OF CORRECTION

PATENT NO. : 5,237,080
DATED : Aug. 17, 1993
INVENTOR(S) : Daute et. al.

It is certified that error appears in the above-indentified patent and that said Letters Patent is hereby corrected as shown below:

In claim 9, column 6, line 54, "ad", should read:
-- and --.

In claim 9, column 6, line 55, "ci-", should read:
-- di- --.

Signed and Sealed this

Thirteenth Day of June, 1995

Attest:

BRUCE LEHMAN

Attesting Officer

Commissioner of Patents and Trademarks